(12) United States Patent
Naya et al.

(10) Patent No.: US 9,575,003 B2
(45) Date of Patent: Feb. 21, 2017

(54) OPTICAL FIELD ENHANCEMENT DEVICE, LIGHT MEASUREMENT APPARATUS AND METHOD

(71) Applicant: FUJIFILM Corporation, Tokyo (JP)

(72) Inventors: Masayuki Naya, Ashigarakami-gun (JP); Shogo Yamazoe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/619,347

(22) Filed: Feb. 11, 2015

(65) Prior Publication Data

US 2015/0153284 A1 Jun. 4, 2015

Related U.S. Application Data

(63) Continuation of application No. PCT/JP2013/004717, filed on Aug. 5, 2013.

(30) Foreign Application Priority Data

Aug. 15, 2012 (JP) .................................. 2012-180009
Feb. 22, 2013 (JP) .................................. 2013-033523

(51) Int. Cl.
*G01N 21/55* (2014.01)
*G01N 21/65* (2006.01)
*G01N 21/01* (2006.01)

(52) U.S. Cl.
CPC ............ *G01N 21/658* (2013.01); *G01N 21/01* (2013.01); *G01N 2201/02* (2013.01); *G01N 2201/06113* (2013.01)

(58) Field of Classification Search
CPC ........ G01N 21/65; G01N 21/63; G01N 21/64; G01N 21/648; G01N 21/658

(Continued)

(56) References Cited

U.S. PATENT DOCUMENTS 4,877,747 A * 10/1989 Stewart ................ G01N 21/553
356/432
5,485,277 A * 1/1996 Foster .................. G01N 21/648
356/445

(Continued)

FOREIGN PATENT DOCUMENTS

JP 5-52740 A 3/1993
JP 2006-514286 A 4/2006

(Continued)

OTHER PUBLICATIONS

Ghadarghadr et al., "Plasmonic array nanoantennas on layered substrates: modeling and radiation characteristics", Optics Express, Oct. 12, 2009, vol. 17, No. 21, pp. 18556-18570.

(Continued)

*Primary Examiner* — Tarifur Chowdhury
*Assistant Examiner* — Isiaka Akanbi
(74) *Attorney, Agent, or Firm* — Birch, Stewart, Kolasch & Birch, LLP

(57) ABSTRACT

An optical field enhancement device that generates an enhanced optical field on a surface of a metal film by an optical field enhancement effect of localized plasmon induced on the surface of the metal film by light projected onto a nanostructure on which the metal film is formed, the device including a transparent substrate having a transparent nanostructure on a surface, a metal film formed on a surface of the nanostructure, and a support member for supporting a subject at a position spaced apart from the surface of the metal film.

13 Claims, 3 Drawing Sheets

(58) Field of Classification Search
USPC ...... 356/317–318, 445, 301, 244; 250/458.1, 250/459.1
See application file for complete search history.

(56) References Cited

U.S. PATENT DOCUMENTS

| | | | | |
|---|---|---|---|---|
| 5,577,137 | A | * | 11/1996 | Groger ............... G01N 21/6428 250/227.11 |
| 6,236,033 | B1 | * | 5/2001 | Ebbesen ............... B82Y 20/00 250/216 |
| 6,776,962 | B1 | * | 8/2004 | Boss ..................... C03C 17/38 356/301 |
| 8,025,844 | B2 | * | 9/2011 | Uchiyama .......... G01N 21/7703 422/401 |
| 2004/0161369 | A1 | | 8/2004 | Chan et al. |
| 2008/0037022 | A1 | * | 2/2008 | Nishikawa ........... G01N 21/554 356/445 |
| 2009/0027668 | A1 | * | 1/2009 | Fujimaki ............... G01N 21/65 356/301 |
| 2010/0240144 | A1 | | 9/2010 | Gilbert |
| 2010/0315628 | A1 | | 12/2010 | Mertsching et al. |
| 2013/0182248 | A1 | * | 7/2013 | Naya .................... G01N 21/648 356/301 |
| 2013/0182343 | A1 | | 7/2013 | Naya et al. |
| 2014/0034235 | A1 | | 2/2014 | Yamazoe et al. |
| 2014/0152801 | A1 | * | 6/2014 | Fine ...................... H04N 7/18 348/79 |

FOREIGN PATENT DOCUMENTS

| | | |
|---|---|---|
| JP | 2009-531696 A | 9/2009 |
| JP | 2010-509601 A | 3/2010 |
| JP | 2011-180043 A | 9/2011 |
| JP | 2012-63293 A | 3/2012 |
| JP | 2012-211839 A | 11/2012 |

OTHER PUBLICATIONS

International Search Report, issued in PCT/JP2013/004717, dated Dec. 24, 2013.
Pakizeh et al., "Unidirectional Ultracompact Optical Nanoantennas", Nano Letters, 2009, vol. 9, No. 6, pp. 2343-2349.
Toda et al., "Enhancement of Positive Hole Injection to Liquid-Crystalline Semiconductor from Au Electrode Surface-Modified by Thiols", The Journal of the Society of Scientific Photography of Japan, 2007, vol. 70, No. 1, pp. 38-43.
Written Opinion of the International Searching Authority, issued in PCT/JP2013/004717, dated Dec. 24, 2013.
Japanese Office Action, issued Oct. 27, 2015, for Japanese Application No. 2013-033523, along with an English translation.
Japanese Notification of Reasons for Refusal for Japanese Application No. 2013-033523, dated May 31, 2016, with Machine translation.
Japanese Notification of Reasons for Refusal issued in the corresponding Japanese Patent Application No. 2013-033523, dated Dec. 14, 2016, with an English Translation thereof.

* cited by examiner

OPTICAL FIELD ENHANCEMENT DEVICE, LIGHT MEASUREMENT APPARATUS AND METHOD

CROSS-REFERENCE TO RELATED APPLICATIONS

This application is a Continuation of PCT International Application No. PCT/JP2013/004717 filed on Aug. 5, 2013, which claims priority under 35 U.S.C. §119 (a) to Japanese Patent Application No. 2012-180009 field on Aug. 15, 2012 and Japanese Patent Application No. 2013-033523 field on Feb. 22, 2013, the contents of which are hereby expressly incorporated herein by reference in their entirety.

TECHNICAL FIELD

The present invention relates to an optical field enhancement device having a metal nanostructure for inducing localized plasmon, and a light measurement apparatus and method for measuring light enhanced by the use of the optical field enhancement device.

BACKGROUND ART

Heretofore, optical field enhancement devices, such as sensor devices and Raman spectroscopy devices, which utilize an optical field enhancement effect of a localized plasmon resonance phenomenon on a metal surface have been known. The Raman spectroscopy is a method for obtaining a Raman scattered light spectrum (Raman spectrum) by separating scattered light obtained by projecting single wavelength light onto a substance, and it is used for identifying a substance and the like.

The Raman spectroscopy includes a method called surface-enhanced Raman spectroscopy (SERS) that utilizes an optical field enhanced by localized plasmon resonance in order to enhance weak Raman scattered light (refer to PCT Japanese Publication No. 2006-514286, Japanese Unexamined Patent Publication No. 2012-211839, T. Toda et al., "Enhancement of Positive Hole Injection to Liquid-Crystalline Semiconductor from Au Electrode Surface-Modified by Thiols", The Journal of the Society of Scientific Photography of Japan, Vol. 70, No. 1, pp. 38-43, 2007, S. Ghadarghadr et al., "Plasmonic array nanoantennas on layered substrates: modeling and radiation characteristics", Optics Express, Vol. 17, No. 21, pp. 18556-18570, 2009 and T. Pakizeh and M. Kaell, "Unidirectional Ultracompact Optical Nanoantennas", Nano Letters, Vol. 9, No. 6, pp. 2343-2349, 2009).

This makes use of the principle that if light is projected onto a metal body, in particular, onto a metal body having a nano-order uneven pattern on a surface with a substance being in contact with the surface, optical field enhancement occurs due to localized plasmon resonance and the intensity of Raman scattered light of the sample in contact with the surface of the metal body is enhanced.

More specifically, the surface-enhanced Raman spectroscopy may be implemented using, for example, a substrate having a metal nanostructure on a surface, placing a subject on the metal film of the substrate, and projecting excitation light onto the place where the object is placed.

When measuring a Raman spectrum of a metabolite discharged from a subject of a living body, for example, if the subject is directly placed on the metal film, however, cells may possibly die out by the bactericidal action of silver or the like and the subject may be destroyed. Further, the metabolite discharged from the subject may not sufficiently diffuse and adhere on the metal film hindered by the subject itself placed directly on the metal film, thereby posing a problem that the Raman spectrum of the metabolite cannot be measured with a high degree of accuracy.

In view of the circumstances described above, it is an object of the present invention to provide an optical field enhancement device capable of holding a subject, such as a living body or the like, without destroying cells of the subject and measuring a Raman spectrum of a substance discharged from the subject and the like with a high degree of accuracy. It is a further object of the present invention to provide a light measurement apparatus and method with the use of the optical field enhancement device.

An optical field enhancement device of the present invention includes a transparent substrate having a transparent nanostructure on a surface and a metal film formed on a surface of the nanostructure on the surface of the substrate, and generates an enhanced optical field on a surface of the metal film by an optical field enhancement effect of localized plasmon induced on the surface of the metal film by light projected onto the nanostructure on which the metal film is formed, wherein the device includes a support member for supporting a subject at a position spaced apart from the surface of the metal film.

In the optical field enhancement device of the present invention described above, the support member may be a member that transmits a substance discharged from the subject.

Further, the device may include a liquid holding section for holding a liquid on the metal film.

Still further, the support member may be a member that transmits a metabolite discharged from the subject of a living body.

Further, the support member may be formed of a porous filter.

Still further, the support member may be a member having a plurality of through holes formed therein.

Further, a void may be provided between the support member and the metal film.

Still further, the nanostructure may be made of boehmite.

Further, the metal film may be made of gold or silver.

A light measurement apparatus of the present invention includes the optical field enhancement device described above, a light projection section for projecting excitation light onto the metal film of the optical field enhancement device, and a light detection section for detecting light generated by the projection of the excitation light onto the optical field enhancement device and outputted from the transparent substrate side.

The light measurement apparatus described above may include a scanning mechanism for two-dimensionally scanning the surface of the metal film of the optical field enhancement device with the excitation light.

A light measurement method of the present invention includes the steps of projecting excitation light onto the metal film of the optical field enhancement device described above, and detecting light generated by the projection of the excitation light onto the optical field enhancement device and outputted from the transparent substrate side.

According to the optical field enhancement device of the present invention, a support member is provided in an optical field enhancement device having a transparent substrate with a transparent nanostructure on the surface and a metal film formed on the surface of the nanostructure formed on the surface thereof to support the subject at a position spaced apart from the surface of the metal film. This results in that the subject never contacts with the metal film directly and cells of the subject are prevented from dying out.

Further, if a support member that transmits a substance discharged from the subject is used as the support member, the substance discharged from the subject may reach the metal film by transmitting through the support member, whereby Raman spectrum of the substance near the metal film or the like to be measured with a high degree of accuracy.

Still further, in the optical field enhancement device of the present invention described above, if a liquid holding section for holding a solution is provided on the metal film, the substance discharged from the subject may be diffused sufficiently in the solution and a sufficient amount of the substance may be attached to the metal film.

BEST MODE FOR CARRYING OUT THE INVENTION

Figure 1:
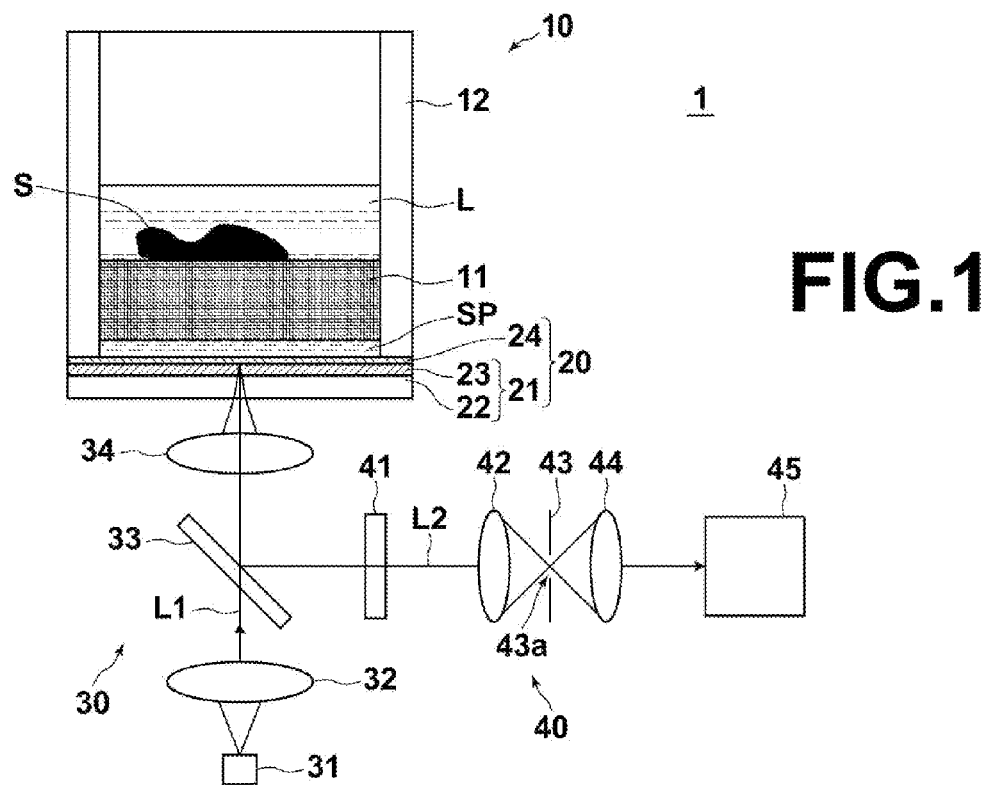
FIG. 1 shows a Raman scattered light measurement apparatus that uses one embodiment of the optical field enhancement device and the light measurement apparatus of the present invention, schematically illustrating the configuration thereof.

Hereinafter, a Raman scattered light measurement apparatus that uses one embodiment of the light measurement apparatus and method of the present invention will be described in detail with reference to the accompanying drawings. FIG. 1 is a block diagram of a Raman scattered light measurement apparatus 1 of the present embodiment, illustrating the schematic configuration thereof.

As shown in FIG. 1, the Raman scattered light measurement apparatus 1 includes an optical field enhancement device 10 in which a subject S is placed, an excitation light projection section 30 for projecting excitation light L1 from the rear side (transparent substrate side) of an optical field enhancement substrate 20 of the optical field enhancement device 10, and a light detection section 40 for detecting Raman scattered light L2 generated from a substance near a metal film 24 of the optical field enhancement substrate 20 and enhanced by the action of the optical field enhancement substrate 20 from the rear side of the optical field enhancement substrate 20.

The optical field enhancement device 10 will be described first. As illustrated in FIG. 1, the optical field enhancement device 10 of the present embodiment includes the optical field enhancement substrate 20, a liquid holding section 12 for holding a liquid L on the metal film 24 of the optical field enhancement substrate 20, and a support member 11, provided in the liquid holding section 12, for supporting the subject S at a position spaced apart from the metal film 24 and transmitting a substance discharged from the subject S.

Figure 2A:
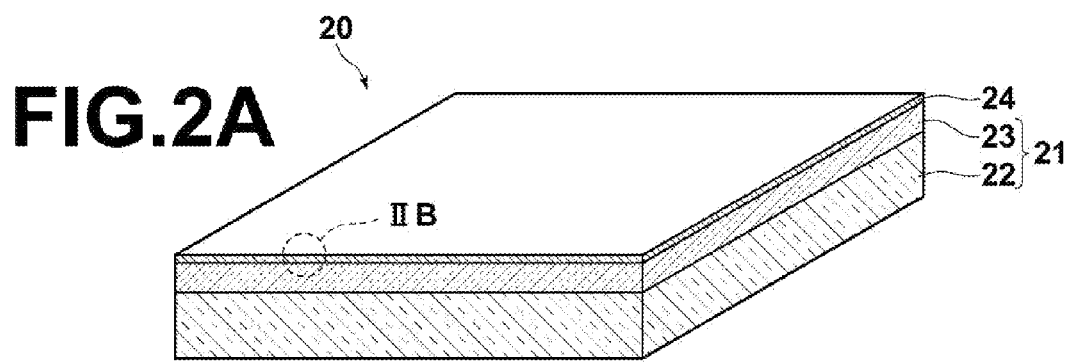
FIG. 2A is a perspective view of an optical field enhancement substrate of an optical field enhancement device provided in the Raman scattered light measurement apparatus shown in FIG. 1.
Figure 2B:
FIG. 2B is an enlarged view of a portion (II B) of a lateral face of the optical field enhancement substrate shown in FIG. 2A.

FIG. 2A is a perspective view of only the optical field enhancement substrate 20 of the optical field enhancement device 10, and FIG. 2B is an enlarged view of a portion II B of a lateral face of the optical field enhancement substrate 20 shown in FIG. 2A.

As shown in FIGS. 2A and 2B, the optical field enhancement substrate 20 includes a transparent substrate 21 with a nanostructure 23 formed on the surface and a metal film 24 formed on the surface of the nanostructure 23. A metal nanostructure is formed by forming the metal film 24 along the nanostructure 23.

The optical field enhancement substrate 20 induces localized plasmon resonance when the excitation light L1 is projected onto the nanostructure 23 on which the metal film 24 is formed (metal nanostructure) and generates an enhanced optical field on the surface of the metal film 24 by the localized plasmon resonance.

The transparent substrate 21 is formed of a transparent substrate body 22 and a nanostructure 23 made of a material different from that of the transparent substrate body 22.

The nanostructure 23 of the present embodiment is made of boehmite The nanostructure 23 is formed such that the average of the depths and the average of the pitches of the convex portions of the metal nanostructure after the metal film 24 is formed on the surface are shorter than the wavelength of the excitation light L1, but the structure may be formed in any manner as long as it can cause localized plasmon resonance on the metal nanostructure. In particular, the nanostructure 23 preferably has an average depth from the apex of a convex portion to the bottom of an adjacent concave portion less than or equal to 200 nm and an average pitch between the apexes of the nearest neighboring convex portions across a concave portion less than or equal to 200 nm.

The metal film 24 may be made of any metal as long as it can cause localized plasmon by receiving excitation light but it is made of at least one kind of metal selected from a group consisting of, for example, Au, Ag, Cu, Al, Pt, and alloys based on these metals. In particular, Au or Ag is preferable.

There is not any specific restriction on the film thickness of the metal film 24 as long as it can maintain an uneven shape, when formed on the surface of the nanostructure 23, capable of generating localized plasmon as the metal nanostructure by receiving excitation light, but the thickness is preferably 10 to 100 nm.

Figure 3:
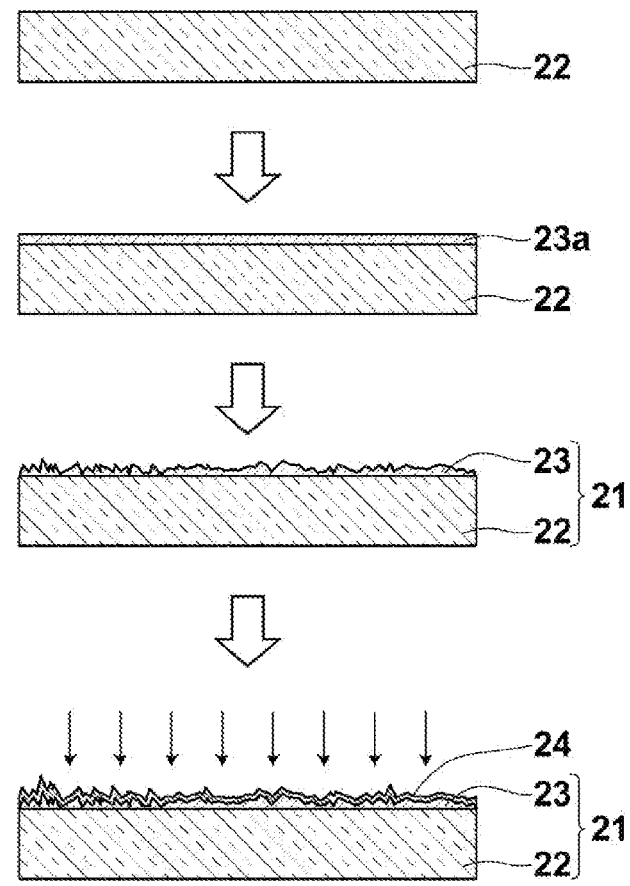
FIG. 3 shows cross-sectional views of an optical field enhancement substrate at each process step, illustrating a manufacturing method thereof.

A manufacturing method of the optical field enhancement substrate 20 in the present embodiment will now be described using FIG. 3. FIG. 3 shows cross-sectional views of the optical field enhancement substrate 20 at each process step.

First, a plate-like transparent substrate body 22 is prepared. The transparent substrate body 22 is washed with pure water. Thereafter, aluminum 23a is formed on the surface of the transparent substrate body 22 by sputtering with a thickness of about several tens of nanometers.

Thereafter, the transparent substrate body 22 with the aluminum 23a is immersed in boiling pure water and taken out after several minutes (about five minutes). This boil treatment (boehmite treatment) causes the aluminum 23a to be transparent and a nanostructure 23 is formed. A metal film 24 is vapor-deposited on the nanostructure 23. The foregoing processes produce an optical field enhancement substrate 20.

Note that the metal film 24 may be formed not only by vapor deposition but also, for example, by immobilizing metal fine particles.

Further, the metal subjected to the hydrothermal reaction in the foregoing nanostructure manufacturing process by boil treatment may be a metal oxide, such as alumina ($Al(OH)_3$), instead of the aluminum described above. Aluminum and alumina allow a nanostructure having a complicated triangular pyramid of either or both of bayerite ($Al[OH]_3$) and boehmite (AlOOH) to be formed on a substrate by subjecting to hydrothermal reaction. Other metals that may form a nanostructure by hydrothermal reaction, such as titanium (Ti) and the like, may also be used, in addition to aluminum.

The method of forming a metal or metal oxide film on the transparent substrate body 22 is not limited to sputtering and heating deposition method or sol-gel method may be used.

The hydrothermal reaction is not limited to the boil treatment and a substrate with a metal or metal oxide film formed thereon may be exposed to high temperature water vapor to react the metal or metal oxide with the water vapor.

Then, a liquid holding section 12 having a cylindrical side wall with the optical field enhancement substrate 20 as the bottom face is provided on the metal film 24 of the optical field enhancement substrate 20. The liquid holding section 12 maintains a living body subject S so that the cells of the subject do not die out, and retains a solution L for diffusing a substance discharged from the subject S. As for the solution L held in the liquid holding section 12 may be, for example, phosphate buffered saline (PBS).

Further, the liquid holding section 12 includes therein a support member 11 for supporting a subject S like that described above. The support member 11 of the present embodiment is formed of, for example, a porous filter having a multitude of micro or sub-micro pores.

Such porous filter have a thickness of about several tens of micrometers to several hundreds of micrometers, and is formed of a resin, such as polystyrene, or ceramic. More specifically, for example, polycarbonate ISOPORE® Membrane filter (Millipore Corporation), hydrophilic PTFE (polytetrafluoroethylene) OMNIPORE®, mixed cellulose ester MF-Millipore™, hydrophilic PVDF (polyvinylidene fluoride) Durapore™, inorganic alumina Anodisc™, and the like are preferably used.

In a case in which cells are cultured on the support member 11, the support member 11 is preferably sterilized, for example, by autoclave treatment or the like. Further, commercially available membrane wells for cell culture, such as sterilized Intercell™ (Cosmo Bio Co., Ltd) may also be used.

The support member 11 formed of the porous filter can maintain the living body subject S so that cells of the subject do not die out and culture cells, in addition to transmitting a substance, such as a metabolite, discharged from the subject S. The subject S placed on the support member 11 discharges a metabolite when a subject stimulant is added to the solution L held in the liquid holding section 12, and the metabolite reaches near the surface of the metal film 24 of the optical field enhancement substrate 20 by transmitting through the support member 11. This results in that Raman scattered light of the metabolite is measured. The metabolite discharged from the subject S may include, for example, ATP (adenosine triphosphate), Ca (calcium), and the like.

The upper limit of the preferable range of the pore diameters of the porous filter is preferably 1 µm or less from the viewpoint that cell sizes are generally in the range of 1 µm to 100 µm, and 2 nm or greater in that it allows metabolites, such as ATP (adenosine triphosphate), Ca (calcium), and the like to pass through easily. The range of 0.03 µm to 1 µm is more preferable from the viewpoint of obtainability.

The support member 11 formed of the porous filter also retains foreign particles other than the substance discharged from the subject S.

In the present embodiment, a void SP is provided between the support member 11 and the metal film 24 of the optical field enhancement substrate 20, as shown in FIG. 1. The void SP is provided to allow a metabolite or the like transmitted through the support member 11 to be sufficiently diffused in the solution L of the void SP. The void SP is provided, for example, at a spacing of 1 µm to 5 mm. Further, a configuration may be adopted in which the void is depressurized, as required, to allow a metabolite to transmit through the support member 11 formed of the porous filter easily.

The excitation light projection section 30 includes a semiconductor laser light source 31 that emits excitation light L1, a half mirror 33 that transmits the excitation light L1 emitted from the semiconductor laser light source 31 and reflects light which includes Raman scattered light L2 emitted from a substance near the metal film 24 of the optical field enhancement substrate 20 by the projection of the excitation light L1 onto the light detection section 40 side, and a lens 34 that focuses the excitation light L1 transmitted through the half mirror 33 near the metal film 24 of the optical field enhancement substrate 20, and collimates the Raman scattered light L2.

The light detection section 40 includes a notch filter 41 that removes excitation light L1 contained in the light reflected by the half mirror 33 and transmits the rest of the light, a pinhole plate 43 having a pinhole 43a for removing noise light, a lens 42 for focusing the enhanced Raman scattered light L2 emitted from the substance near the metal film 24 of the optical field enhancement substrate 20 and transmitted through the lens 34 and the notch filter 41 on the pinhole 43a, a lens 44 for collimating the Raman scattered light L2 passed through the pinhole 43a, and a spectroscope 45 for detecting the Raman scattered light.

Next, a method for measuring a Raman spectrum of a metabolite discharged from a subject S or the like with the use of the Raman scattered light measurement apparatus 1 of the present embodiment will be described.

First, the subject S is placed on the support member 11 of the optical field enhancement device 10 and a solution L is retained in the liquid holding section 12 such that the subject S is immersed.

Then, excitation light L1 is emitted from the semiconductor laser light source 31 of the excitation light projection section 30, which is transmitted through the half mirror 33, then focused by the lens 34, and projected near the metal film 24 of the optical field enhancement substrate 20.

Localized plasmon resonance is induced in the metal nanostructure of the optical field enhancement substrate 20 and an enhanced optical field is generated on the surface of the metal film 24. Raman scattered light L2 emitted from a substance near the metal film 24 and enhanced by the optical field is transmitted through the lens 34 and reflected by the half mirror 33 onto the spectroscope 45 side. Note that excitation light L1 reflected from the optical field enhancement substrate 20 is also reflected by the half mirror 33 onto the spectroscope 45 side, but the excitation light L1 is removed by the notch filter 41.

In the meantime, light having a different wavelength from that of the excitation light L1 is transmitted through the notch filter 41 and focused on the pinhole 43a. The light transmitted through the pinhole 43a is collimated by the lens 44 and inputted to the spectroscope 45. Note that, in the Raman scattered light measurement apparatus 1 of the present embodiment, Rayleigh scattered light, Mie scattered light, or the like is cut by the notch filter 41 and never entered in the spectroscope 45, as they have the same wavelength as that of the excitation light L1. The Raman scattered light L2 is inputted to the spectroscope 45 and Raman spectrum measurement is performed.

According to the Raman scattered light measurement apparatus 1 of the foregoing embodiment, a support member 11 is provided in an optical field enhancement device 10 having a transparent substrate 21 with a transparent nanostructure on the surface and a metal film 24 formed on the surface of the nanostructure formed on the surface thereof to support the subject S at a position spaced apart from the surface of the metal film 24 and to transmit a substance discharged from the subject S. This results in that the subject never contacts with the metal film directly and cells of the subject are prevented from dying out, and allows a substance discharged from the subject S to reach the metal film by transmitting through the support member 11, whereby Raman spectrum of the substance near the metal film 24 or the like to be measured with a high degree of accuracy.

Further, as a liquid holding section 12 for holding a solution L is provided on the metal film 24, the substance discharged from the subject S may be diffused sufficiently in the solution L and a sufficient amount of the substance may be attached to the metal film 24.

In the Raman scattered light measurement apparatus 1 of the foregoing embodiment, an optical field enhancement substrate 20 having a transparent substrate 21 is used. Even in a case in which the support member 11 is made of an opaque material, this allows input of excitation light L1 and detection of Raman scattered light L2 to be implemented from the surface on the transparent substrate side of the optical field enhancement substrate 20.

Figure 4:
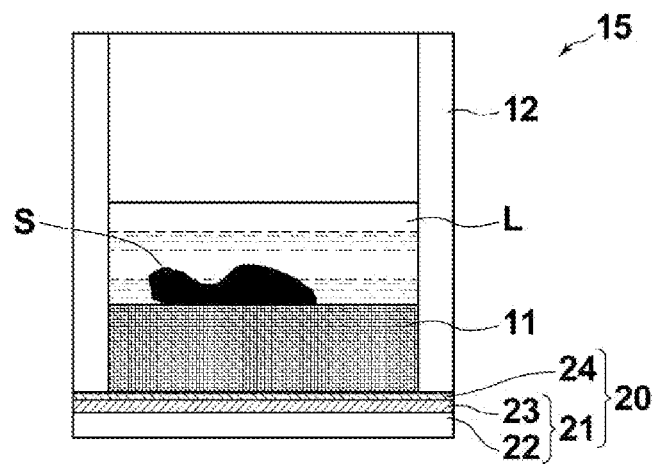
FIG. 4 shows another embodiment of the optical field enhancement device.

Further, in the foregoing embodiment, a void SP is provided between the metal film 24 of the optical field enhancement substrate 20 and the support member 11 in the optical field enhancement device 10, but the support member 11 may be provided directly on the metal film 24, as in an optical field enhancement device 15 shown in FIG. 4.

Direct provision of the support member 11 on the metal film 24 in this way allows a metabolite discharged from the subject to reach the metal film 24 almost immediately below by transmitting through the support member 11. Therefore, for example, if a Raman spectrum is measured by scanning the excitation light two-dimensionally, as will be described later, the two-dimensional distribution of a metabolite discharged from the subject S may be measured with a high degree of accuracy.

If the support member 11 is provided directly on the metal film 24, a Raman spectrum of the support member 11 itself is likely to be mixedly present depending the degree of adhesion between the support member 11 and the metal film 24, but such spectrum may be removed, for example, by signal processing.

Figure 5:
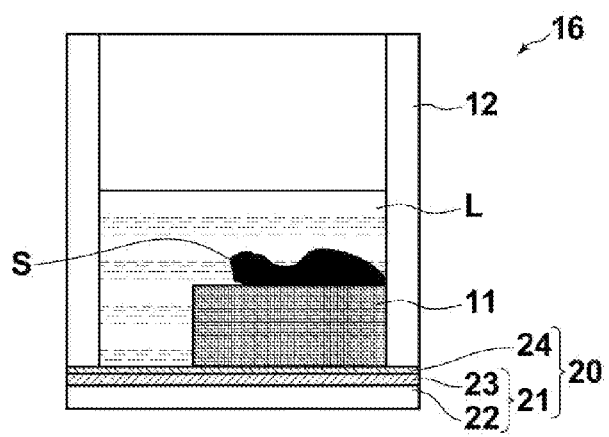
FIG. 5 shows still another embodiment of the optical field enhancement device.

Further, a support member 11 may be provided on a portion of the metal film 24 and a subject S may be placed on the support member 11, as in the optical field enhancement device 16 shown in FIG. 5, instead of providing a support member 11 on the entire surface of the metal film 24, as in the optical field enhancement device 15 shown in FIG. 4.

In the case in which the support member 11 is provided in the foregoing manner, if an arrangement is adopted in which a Raman spectrum of a metabolite or the like diffused near the metal film 34 on which no support member 11 is provided, the support member 11 is not necessarily made of a material that transmits a substance discharged from the subject S. More specifically, for example, a plate member made of gelatin may be used. This may increase the freedom of material selection for the support member 11 and the support member 11 may hold various types of subjects without destroying them.

Figure 6:
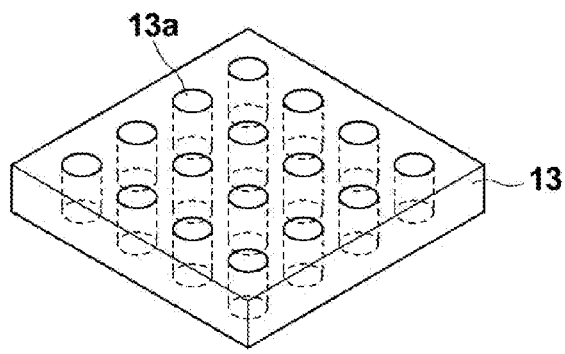
FIG. 6 shows another embodiment of a support member in the optical field enhancement device.

Although a porous filter is used as the material that transmits a substance discharged from the subject S in the optical field enhancement devices 10, 15, and 16 of the foregoing embodiments, but not limited to the porous filter and, for example, a plate member 13 having a multitude of through holes 13a, as illustrated in FIG. 6, may be used as a support member. In short, any support member may be used as long as it is made of a material that maintains a living body subject S without destroying it and may transmit a substance discharged from the subject S to the metal film 24 of the optical field enhancement substrate 20.

Further, in the Raman scattered light measurement apparatus 1 described above, an arrangement may be adopted in which the subject S is scanned two-dimensionally with the excitation light L1 and a Raman spectrum is measured at each scanned point on the subject S scanned with the excitation light L1.

Figure 7:
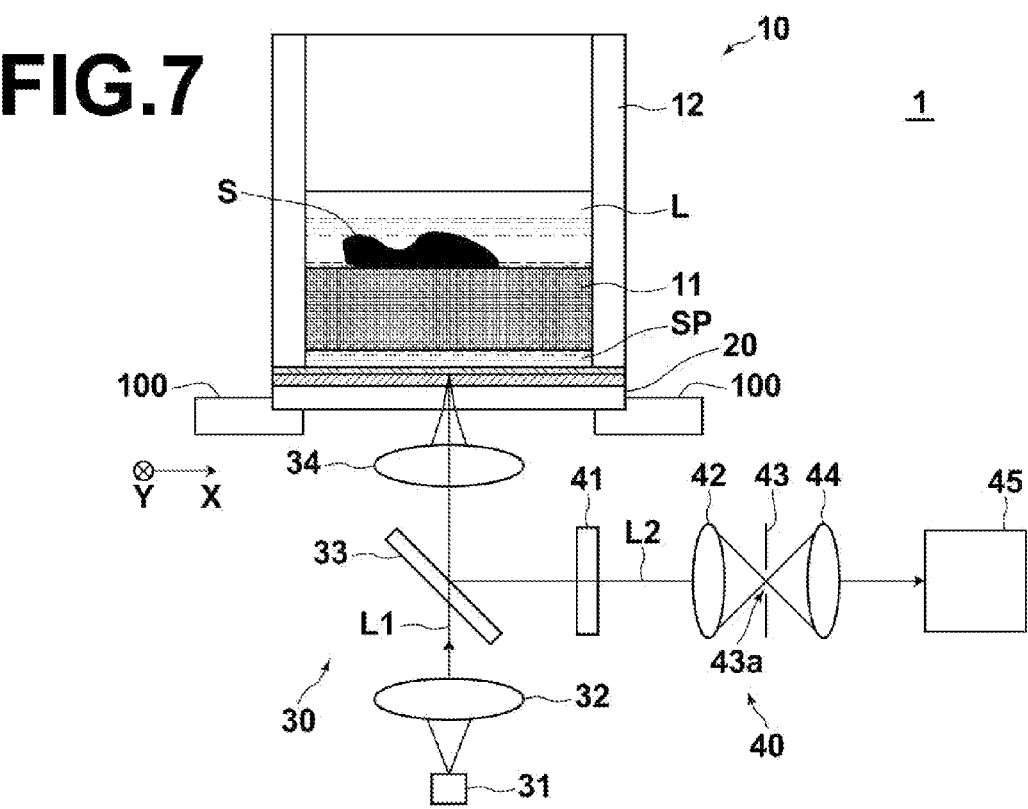
FIG. 7 illustrates a movable stage for moving the optical field enhancement device provided in the Raman scattered light measurement apparatus shown in FIG. 1.

More specifically, as illustrated in FIG. 7, for example, a movable stage 100 (corresponding to the scanning mechanism) that holds the optical field enhancement device 10 and moves the optical field enhancement device 10 in the X direction and the Y direction (thickness direction of the drawing) in FIG. 7 may be provided in the Raman scattered light measurement apparatus 1, and the optical field enhancement device 10 is moved by the movable stage 100 to two-dimensionally scan near the meal film 24 of the optical field enhancement substrate 20 with the excitation light L1.

Note that the scanning mechanism for two-dimensionally scanning the excitation light L1 is not limited to this, and an arrangement may be adopted in which the optical field enhancement device 10 is fixed and near the metal film 24 of the optical field enhancement substrate 20 is two-dimensionally scanned with the excitation light L1 with the use of, for example, a galvanomirror.

In the foregoing embodiments, the nanostructure 23 of the transparent substrate 21 of the optical field enhancement substrate 20 is made of boehmite, but it may be made of a transparent material other than boehmite. For example, a nanostructure 23 may be formed by performing anodization on an aluminum substrate to produce, in an upper layer, anodized alumina having a multitude of fine pores and removing the unanodized aluminum portion, and a transparent substrate 21 may be formed by fixing nanostructure 23 on a transparent substrate body 22, such as glass.

Further, the nanostructure is not limited to that formed of a material different from that of the transparent substrate body, and may be formed of the same material by processing the surface of the transparent substrate body. For example, lithography and dry etching processes may be performed on the surface of a glass substrate to form a nanostructure on the surface and use the glass substrate with the nanostructure formed thereon as the transparent substrate.

As one embodiment of the light measurement apparatus and method of the present invention, a Raman scattered light measurement apparatus and method has been described, but the light measurement apparatus and method of the present invention may also be applied to a plasmon enhanced fluorescence detection method and a fluorescence detection apparatus. In the fluorescence detection apparatus, the optical field enhancement device 10, 15, or 16 is used to place a subject S on the support member 11 and to project excitation light from the transparent substrate side, whereby enhanced fluorescence may be detected from the rear side.

Further, the optical field enhancement devices 10, 15, and 16 may be used in light measurement apparatuses and methods for measuring not only the Raman scattered light and fluorescence, but also for measuring Rayleigh scattered light, Mie scattered light, second harmonic, and the like generated from a substance near the metal film 24 illuminated by the excitation light L1, in which a subject S is placed on the support member 11 and excitation light is projected from the transparent substrate side, whereby enhanced light may be detected from the rear side, as in the manner described above.

What is claimed is:

1. An optical field enhancement device that generates an enhanced optical field on a surface of a metal film by an optical field enhancement effect of localized plasmon induced on the surface of the metal film by light projected onto a nanostructure on which the metal film is formed, the device comprising:
   a transparent substrate having a transparent nanostructure on a surface;
   a metal film formed on a surface of the nanostructure;
   a liquid folding portion for holding a liquid, provided above the metal film in the vertical direction; and
   a support member provided within the liquid holding portion for supporting a subject at a position spaced apart above the metal film in the vertical direction.

2. The optical field enhancement device as claimed in claim 1, wherein the support member transmits a substance discharged from the subject.

3. The optical field enhancement device as claimed in claim 1, wherein the device comprises a liquid holding section for holding a liquid on the metal film.

4. The optical field enhancement device as claimed in claim 1, wherein the support member transmits a metabolite discharged from the subject of a living body.

5. The optical field enhancement device as claimed in claim 1, wherein the support member is formed of a porous filter.

6. The optical field enhancement device as claimed in claim 1, wherein the support member has a plurality of through holes formed therein.

7. The optical field enhancement device as claimed in claim 1, wherein a void is provided between the support member and the metal film.

8. The optical field enhancement device as claimed in claim 1, wherein the nanostructure is made of boehmite.

9. The optical field enhancement device as claimed in claim 1, wherein the metal film is made of gold or silver.

10. A light measurement apparatus, comprising:
    the optical field enhancement device as claimed in claim 1;
    a light projection section for projecting excitation light onto the metal film of the optical field enhancement device; and
    a light detection section for detecting light generated by the projection of the excitation light onto the optical field enhancement device and outputted from the transparent substrate side.

11. The light measurement apparatus as claimed in claim 10, wherein the apparatus comprises a scanning mechanism for two-dimensionally scanning the surface of the metal film of the optical field enhancement device with the excitation light.

12. A light measurement method, comprising the steps of:
    projecting excitation light onto the metal film of the optical field enhancement device as claimed in claim 1; and
    detecting light generated by the projection of the excitation light onto the optical field enhancement device and outputted from the transparent substrate side.

13. An optical field enhancement device as defined in claim 1, wherein:
    the support member is provided within the liquid holding portion along with the liquid.

* * * * *